(12) United States Patent
Dosta et al.

(10) Patent No.: US 9,763,752 B2
(45) Date of Patent: Sep. 19, 2017

(54) DENTAL IMPLANT HAVING POROUS STRUCTURE

(71) Applicant: ALTIMED International SA, Geneva (CH)

(72) Inventors: Anatoli D. Dosta, Minsk (BY); Aliaksandr I. Halauko, Minsk (BY); Dmitri A. Dosta, Minsk (BY)

(73) Assignee: Joint Stock Company 'ALTIMED', Osipovichi (BY)

( * ) Notice: Subject to any disclaimer, the term of this patent is extended or adjusted under 35 U.S.C. 154(b) by 0 days.

(21) Appl. No.: 14/935,638

(22) Filed: Nov. 9, 2015

(65) Prior Publication Data

US 2016/0058530 A1 Mar. 3, 2016

Related U.S. Application Data

(63) Continuation of application No. PCT/IB2013/000971, filed on May 7, 2013.

(51) Int. Cl.
*A61C 8/00* (2006.01)
*A61B 6/02* (2006.01)
*A61B 6/14* (2006.01)

(52) U.S. Cl.
CPC .............. *A61C 8/0037* (2013.01); *A61B 6/02* (2013.01); *A61B 6/14* (2013.01); *A61C 8/0012* (2013.01);
(Continued)

(58) Field of Classification Search
CPC ... A61C 8/0037; A61C 8/0012; A61C 8/0019; A61C 8/0036; A61C 8/0022;
(Continued)

(56) References Cited

U.S. PATENT DOCUMENTS

| 6,244,868 B1 | 6/2001 | Schappert |
| 2005/0112397 A1 | 5/2005 | Rolfe et al. |

(Continued)

FOREIGN PATENT DOCUMENTS

| BY | 10325 C1 | 2/2008 |
| DE | 19816865 A1 | 10/1999 |

(Continued)

OTHER PUBLICATIONS

International Search Report from International Application No. PCT/IB2013/000971 filed May 7, 2013, mailed Jan. 27, 2014.

(Continued)

*Primary Examiner* — Pedro Philogene
*Assistant Examiner* — David C Comstock
(74) *Attorney, Agent, or Firm* — Patentbar International, P.C.

(57) ABSTRACT

The porous three-dimensional structure of the implant is made as a three-dimensional body with open through pores and one-side open pores distributed evenly on the internal surface of open pores and connected to the internal surface. Sizes of pores are randomly distributed in the range of 150-300 μm. A reinforcing element is made from titanium or titanium alloy as a mesh with the protrusions evenly distributed on the outer surface of the mesh, and is located on the surface of the three-dimensional body. The method of manufacture and method of installation of one of the variants of the dental implant with the possibility of press fit in the jaw bone immediately after extraction of the tooth without arrest of bleeding are based on the porous three-dimensional structure claimed as well.

5 Claims, 2 Drawing Sheets

(52) U.S. Cl.
CPC .......... *A61C 8/0019* (2013.01); *A61C 8/0022* (2013.01); *A61C 8/0036* (2013.01); *A61C 8/0075* (2013.01); *A61C 2008/0046* (2013.01)

(58) Field of Classification Search
CPC . A61C 8/0075; A61C 2008/0046; A61B 6/02; A61B 6/14
USPC ...................................... 433/201.1, 206, 207
See application file for complete search history.

(56) References Cited

U.S. PATENT DOCUMENTS

| 2006/0105295 A1* | 5/2006 | Mayer ..................... | A61B 17/68 433/173 |
| 2009/0042158 A1* | 2/2009 | Steiner ................. | A61C 8/0006 433/7 |
| 2009/0208907 A1* | 8/2009 | Dosta ................... | A61C 8/0009 433/174 |

FOREIGN PATENT DOCUMENTS

| EP | 0296335 A1 | 12/1988 |
| WO | 9721393 A1 | 6/1997 |
| WO | 9724084 A1 | 7/1997 |
| WO | 2008052300 A1 | 5/2008 |
| WO | 2010139041 A1 | 12/2010 |

OTHER PUBLICATIONS

Vityaz P.A. et al, Porous Powder Materials and Products thereof, Vysheyshaya Shkola, 1987, pp. 113-115, 137, Minsk.
Mish, K. E., Orthopedic Treatment with Support on Dental Implants. Moscow, 2010, pp. 347-348.

* cited by examiner

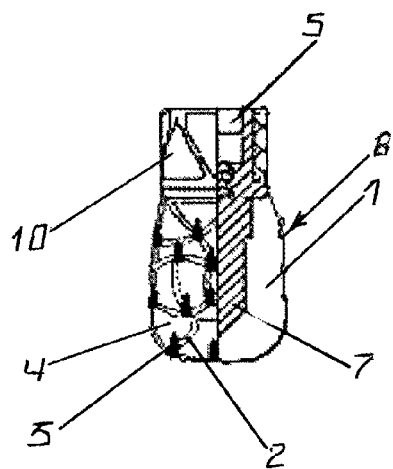
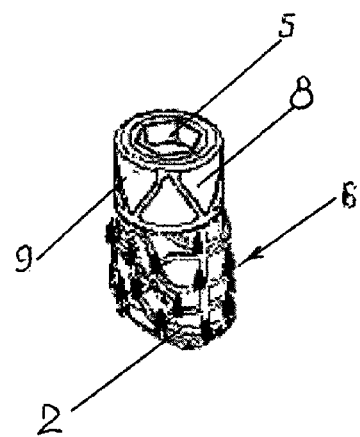
Fig. 1
Fig. 2
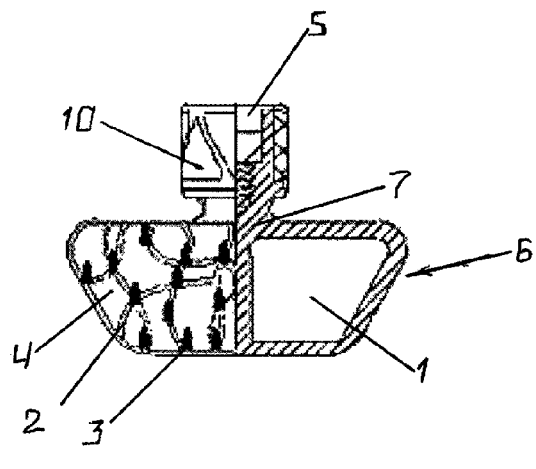
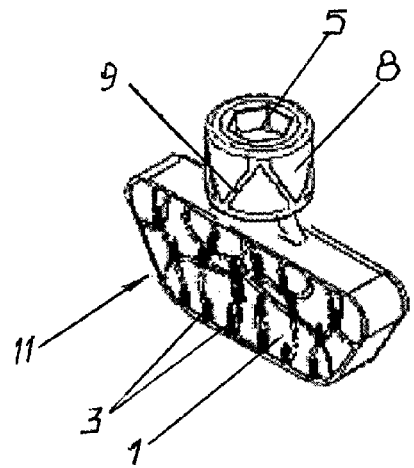
Fig. 3
Fig. 4

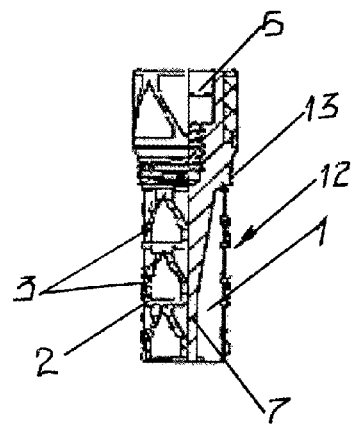
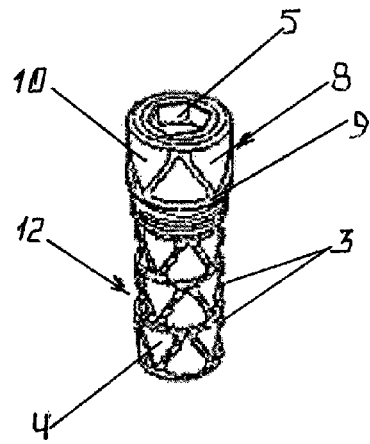
Fig. 5  Fig. 6
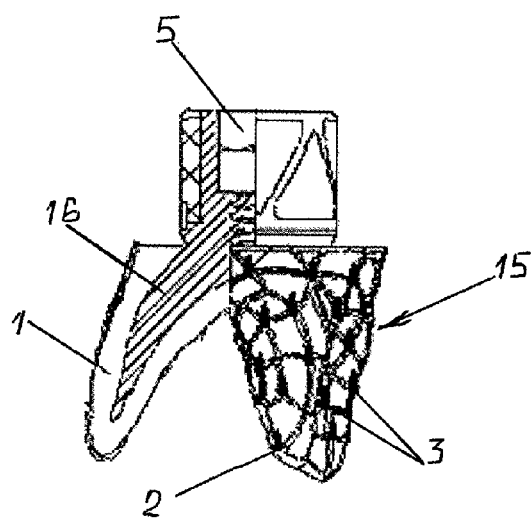
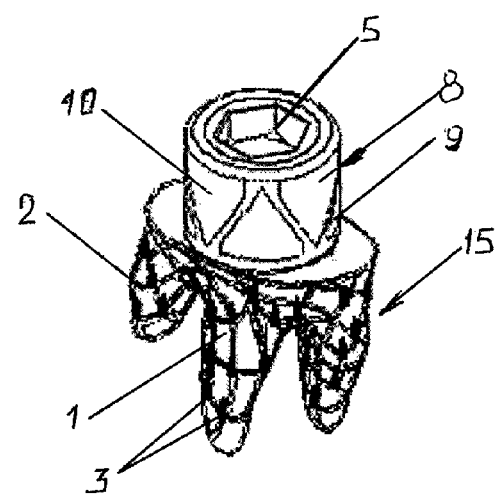
Fig. 7  Fig. 8

DENTAL IMPLANT HAVING POROUS STRUCTURE

RELATED APPLICATIONS

This Application is a Continuation application of International Application PCT/IB2013/000971, filed on May 7, 2013, which is incorporated herein by reference in its entirety.

FIELD OF THE INVENTION

The invention refers to the medical devices and may be used in production of the implants for bone tissue replacement, in particular, in dentistry.

BACKGROUND OF THE INVENTION

Porous three-dimensional structures intended for usage in the medical devices are well-known nowadays.

Such structures may be, for example, a coating applied to a base [EP 0 296 335, publ. on 28.04.1988] or a compressed stack of metal sheets with the apertures which form through regular canals in the structure [US20050112397, publ. on 26.05.2005].

The disadvantages of known structures are discovered in [Karl E. MISH Orthopedic Treatment with Support on Dental Implants. Moscow, 2010, p. 347-348] and are associated with susceptibility to formation of the structure detachment, chipping and burrs.

The solution which is the closest to the technical solution claimed is the porous three-dimensional structure [WO 97/24084, publ. on 10.07.1997] made as a three-dimensional body, containing through pores and one-side open pores which are distributed evenly on the internal surface of open pores and connected to the internal surface, with sizes of pores randomly distributed in the range of 150-300 µm.

Insufficient strength and rigidity are the disadvantages of the known porous three-dimensional structure. As a rule, this structure is made on the base, and the carried out studies have shown the susceptibility to formation of the structure detachment, chipping and burrs.

There is the implant [WO 97/21393 A1, publ. on 19.06.1997] having the surface contacting with the bone tissue, containing the biologically compatible porous metal zone where bone tissue can grow into. However, the effect of this bone integration is ensured by microstructure of the metal surface area only, as the implant construction is a special cylinder without any macrogeometry promoting ingrowth of bone tissues into the implant.

There is the implant [DE 19816865 A1, publ. on 10.07.1997] containing the bioactive silicate glass coating in the zone of contact with the gum. The epithelial cells of gums can grow together with the coating on the implant ensuring its firm fit in the jaw. However, the implant construction promotes the tissue ingrowth only, without stimulation of this process and without prevention from possible ingress of infection in the implantation zone.

There is the dental cylinder-shaped implant with the base made from titanium [WO 2008/52300 A1, publ. on 08.05.2008] containing the cavity for the porous structure and the canal for introduction of medicinal drugs; the implant case is made as an external threadform spiral which is fixed by three longitudinal stiffening ribs installed inside the spiral. This dental implant is the nearest prior art reference of the first and second variants of the implant claimed.

Here the porous structure with pores sizes of 150-300 µm is installed inside the spiral.

There is the dental implant and its installation method [US6244868, publ. on 12.06.2001] being the nearest prior art reference to the third variant of the implant claimed and to the method declared, respectively. The dental implant described has the seat for a dental prosthesis and biologically compatible metal porous zone for contact with bone. The described implant is installed by means of press-fit in the jaw bone immediately after extraction of such tooth without arrest of bleeding. As by this method the dental implant is manufactured with the "averaged" biologically compatible metal porous zone, one has to widen the seat in bone for installation and this leads to the increased blood loss and traumatic operation.

The method described in [Vityaz P. A. et al. Porous Powder Materials and Goods Thereof. Minsk, Vysheyshaya Shkola, 1987, p. 114-115, 137] is the nearest prior art reference to the method claimed of manufacture of the implant claimed; this method includes formation of powder of biocompatible material (titanium or its derivatives) on the material, preferably titanium, base—a framework.

The disadvantages of the known nearest prior art references result from the above-described disadvantages of porous biologically compatible materials: layer detachment, chipping and burrs. These disadvantages of applied porous biologically compatible materials determine shortcomings of the goods made from such materials—insufficient primary stability of dental implants.

SUMMARY OF THE INVENTION

The aim of the invention claimed is to create the porous three-dimensional structure of increased strength ensuring absence of the structure detachment, chipping and burrs when it is placed on the base.

One more aim of the present invention is to create different variants of the dental implant ensuring the high primary stability, high strength of its elements, strength and rate of its osteointegration and possibility of implantation in the appropriate zone of the jaw.

One more aim of the present invention is to create the method of manufacture and method of installation of the dental implant ensuring the high primary stability, high strength of its elements, strength and rate of its osteointegration.

The formulated aim in the porous three-dimensional structure made as a three-dimensional body, containing through pores and one-side open pores which are distributed evenly on the internal surface of open pores and connected to the internal surface, with random sizes of pores in the range of 150-300 µm, equipped with a reinforcing element, made from titanium or titanium alloy, has been solved in this way: the reinforcing element is made as a mesh with the protrusions evenly distributed on the outer surface of the mesh, and is located on the surface of the three-dimensional body.

Each protrusion on the outer surface of the reinforcing element is to be shaped as a rectangular parallelepiped with the thickness corresponding to the thickness of the reinforcing element, or shaped as an arrow.

The reinforcing element may be made both by punching from a titanium sheet or by braiding from titanium wire.

The reinforcing element mesh apertures size is preferably not to be less than the minimal size of the pores mentioned.

The three-dimensional structure is formed from titanium powder.

The three-dimensional structure has a base with titanium powder pressed thereto.

The formulated aim in the first variant of the dental implant having the biologically compatible metal porous zone for contact with bone and the seat for the dental prosthesis has been solved in this way: the metal porous zone for contact with bone is made from the porous three-dimensional structure claimed with possibility of press-fit in the jaw bone.

The biologically compatible metal porous zone for contact with bone may have the shape of a cylinder or truncated cone with cross-section as a circle or ellipse, or the shape of a plate with the protrusions located on the outer surface of the reinforcing element in staggered order.

The formulated aim in the second variant of the dental implant having the biologically compatible metal porous zone for contact with bone and the seat for the dental prosthesis has been solved in this way: the metal porous zone for contact with bone is made from the porous three-dimensional structure claimed in the shape of a cylinder or a cone, with the protrusions located on the outer surface of the reinforcing element spirally, forming a helical line to screw the dental implant in the jaw bone.

The formulated aim in the third variant of the dental implant having the biologically compatible metal porous zone for contact with bone and the seat for the dental prosthesis has been solved in this way: the metal porous zone for contact with bone is made from the porous three-dimensional structure claimed in accordance with preliminary obtained 3D-tomogram of the tooth for which replacement this implant is intended, the shape and sizes coincide exactly with the tooth root shape and sizes.

The formulated aim in the method of manufacture of the dental implant claimed including manufacture of the base and formation of the metal porous zone for contact with bone, has been solved in this way: one shall preliminarily make 3D-tomography of the tooth to be removed, manufacture the three-dimensional model of this tooth root in accordance with the tomogram, form the metal porous zone for contact with bone from the porous three-dimensional structure claimed under such model which shape and sizes coincide exactly with the shape and sizes of the tooth root to be replaced with this implant.

The formulated aim in the method of installation of the dental implant including removal of the tooth and installation of the dental implant manufactured beforehand by means of press-fit in the jaw bone immediately after extraction of such tooth without arrest of bleeding, has been solved in this way: one shall preliminarily make 3D-tomography of the tooth before removal, manufacture the three-dimensional model of this tooth root in accordance with the tomogram, form the biologically compatible metal porous zone from the porous three-dimensional structure claimed under such model which shape and sizes coincide exactly with the shape and sizes of the tooth root removed.

BRIEF DESCRIPTION OF THE DRAWINGS

The essence of the inventions claimed is explained by non-limiting drawings where:

FIG. 1 shows, in the form of a sketch, the view with a partial section of the first example of implementation of the first variant of the dental implant claimed implemented with the porous structure claimed and intended for press-fit.

FIG. 2 shows, in the form of a sketch, the general view of the dental implant claimed represented on FIG. 1.

FIG. 3 shows, in the form of a sketch, the view with a partial section of the other example of implementation of the first variant of the dental implant claimed implemented with the porous structure claimed and intended for press-fit.

FIG. 4 shows, in the form of a sketch, the general view of the dental implant claimed represented on FIG. 3.

FIG. 5 shows, in the form of a sketch, the view with a partial section of the second variant of the dental implant claimed implemented with the porous structure claimed and intended for screw fit.

FIG. 6 shows, in the form of a sketch, the general view of the dental implant claimed represented on FIG. 5.

FIG. 7 shows, in the form of a sketch, the view with a partial section of the third variant of the dental implant claimed implemented with the porous structure claimed and intended for the method of installation thereof claimed.

FIG. 8 shows, in the form of a sketch, the general view of the dental implant claimed represented on FIG. 7.

DETAILED DESCRIPTION OF THE PREFERRED EMBODIMENTS

The porous structure is made in any sizes and shapes in accordance with the requirements of, e.g., dentistry (see FIG. 1). Three-dimensionality and commensurability are essential (i.e. the sizes of the structure in three coordinates must be of the same order). Performance of the structure with open through pores and one-side open pores evenly distributed on the internal surface of open pores and connected to this surface, with sizes of pores randomly distributed in the range of 150-300 μm, is known from [WO 97/24084]. The porous structure 1 is equipped with the reinforcing element 2 made as a mesh from titanium or titanium alloy with the protrusions 3 evenly distributed on the outer surface of the mesh, and is located on the surface of the three-dimensional body.

The reinforcing element 2 may be made, for example, by punching from a titanium sheet or by braiding from titanium wire. Commensurability of sizes of apertures 4 of reinforcing element 2 and sizes of these pores is achieved (i.e., sizes of apertures 4 are not to be less than the sizes of pores).

Each of protrusions 3 on the outer surface of the reinforcing element may be shaped as a rectangular parallelepiped with the thickness corresponding to the thickness of the reinforcing element, or shaped as an arrow.

The porous structure claimed is made from biologically compatible materials, for example, from titanium, titanium alloy or other biologically compatible materials.

These materials, on the one hand, are biologically compatible and easily sterilizable and, on the other hand, have the modulus elasticity close to the modulus of elasticity of the bone tissue, thus enabling to agree the mechanical and strength properties of the implant and regenerated bone tissue to the best advantage.

One can obtain the porous structure claimed by different manufacturing methods, for example, by pressing titanium powder formed from titanium sponge, to the base by the hydrostatic pressing method [Vityaz P. A.] or, for example, by means of formation of powder mixture of biocompatible material (titanium or its derivatives) with pore-former and further sintering [BY10325, publ. on 30.12.2003].

By means of the condition that the size of apertures 4 of the reinforcing element 2 is not to be less than the maximal size of the pores mentioned, one can ensure the through penetrability of the structure 1 for blood flow, thus promoting the improved hydrodynamics of blood flow and, consequently, nourishment of the tissue to be regenerated.

The first example of implementation of the first variant of the dental implant claimed is shown on FIG. 1 to 2. The dental implant is manufactured from the biocompatible material, such as titanium, and has the seat 5 for the dental prosthesis (not shown on drawings) and biologically compatible metal porous zone for contact with bone which is made, in this example, as a cylindrical body 6 for press-fit in the jaw bone. The cylindrical body 6 contains the longitudinal base 7 where the porous three-dimensional structure 1 is pressed to; the reinforcing element 2 is on the surface of the porous three-dimensional structure and the evenly located protrusions 3 are fixed on the external surface of the reinforcing element 2.

The ring head 8 made from the porous three-dimensional structure from porous polytetrafluoroethylene and intended for ingrowth of the gum tissues is situated over the cylindrical body 6 around the seat 5.

The auxiliary reinforcing element 9 is made as a hollow body of revolution with apertures and is located over the ring head 8.

The reinforcing element 9 is made from biologically compatible metal, for example, made from titanium wire by the known method of laser welding or punched from a titanium sheet. The size of apertures 10 of the reinforcing element 9 is not less than the minimal size of pores of the porous three-dimensional structure of the ring head 8.

In the other example of implementation of the first variant of the dental implant claimed, as shown on FIGS. 3 to 4, the dental implant claimed contains the biologically compatible metal porous zone for contact with bone made as a plate 11 from titanium powder pressed to the base 7. The head 8, made in the form of a bush, for ingrowth of the soft tissue of the gum is located over the plate 11 around the seat 5 for the dental prosthesis.

The first variant of the dental implant claimed is to be implanted as follows. One shall press the biologically compatible metal porous zone in the form of a cylinder 6 or a plate 11 in the formed aperture of the jaw bone in such a way that the outer surface of the head 8 coincides with the level of the soft tissues of the gum and shall stitch the soft tissues. The dental prosthesis is installed in the seat 5 in the base 7 after final engraftment of the implant.

Due to the fact that the biologically compatible metal zone contacting with the bone tissue is made as a three-dimensional porous structure 1, ingrowth of the bone tissue occurs in its whole depth, with integration with the mentioned three-dimensional porous structure. Here the biologically compatible metal three-dimensional porous zone 1 is safely protected from damages by the reinforcing element 2, and the protrusions 3 function as anchor elements and prevent the whole implant from displacement and, thus, ensure its primary stability.

In addition, the porous three-dimensional structure 1 is safely protected from ingress of infection from the oral cavity by means of the head 8 from polytetrafluoroethylene which has the porous three-dimensional structure ensuring ingrowth of the soft tissues of the gum.

Manufacturing of the biologically compatible metal porous structure in the form of a body of revolution or a plate ensures the possibility to install the dental implant claimed in different places of the jaw having some place for it.

Thus, the dental implant claimed safely protects the implantation area from ingress of pathogenic microbes from the oral cavity, as well as ensures the in-depth ingrowth of the bone tissue, thus promoting the installation strength and fixation in the jaw bone.

The example of implementation of the second variant of the dental implant claimed is represented on FIG. 5 to 6. The dental implant is made from the biocompatible material, such as titanium, and has the seat 5 for the dental prosthesis and biologically compatible metal porous zone 6 for contact with bone made, in this example, as a cylindrical body 12. This body 12 contains the longitudinal base 7 where the porous three-dimensional structure 1 is pressed to; the reinforcing element 2 is on the surface of the porous three-dimensional structure and the evenly located protrusions 3 are fixed on the external surface of the reinforcing element 2. In this example the protrusions 3 are located on the outer surface of the reinforcing element 2 spirally, forming a helical line to screw the dental implant, namely, body 12, in the jaw bone.

The ring head 8 made from the porous three-dimensional structure from porous polytetrafluoroethylene and intended for ingrowth of the gum tissues is situated over the zone 6 around the seat 5.

The head 8 is made, as described in the first example.

The longitudinal base 7 above the body 12 becomes wider and forms the section 13 below the head 8; on the surface of the section 13 there are several screw protrusions for fixation in the cortical layer.

The second variant of the dental implant claimed is to be implanted as follows. One shall screw the biologically compatible metal porous zone in the form of a cylindrical body 12 in the formed aperture of the jaw bone, using the protrusions 3 as thread sections, in such a way that the outer surface of the head 8 coincides with the level of the soft tissues of the gum and shall stitch the soft tissues. The dental prosthesis is installed in the seat 5 in the base 7 after final engraftment of the implant.

Due to the fact that the biologically compatible metal zone contacting with the bone tissue is made as a three-dimensional porous structure 1, ingrowth of the bone tissue occurs in its whole depth, with integration with the mentioned three-dimensional porous structure. Here the biologically compatible metal three-dimensional porous zone 1 is safely protected from damages by the reinforcing element 2, and the protrusions 3 function both as thread sections and anchor elements and prevent the whole implant from displacement and, thus, ensure its primary stability.

In addition, the porous three-dimensional structure 1 is safely protected from ingress of infection from the oral cavity by means of the head 8 from polytetrafluoroethylene which has the porous three-dimensional structure ensuring ingrowth of the soft tissues of the gum.

Thus, the dental implant claimed safely protects the implantation area from ingress of pathogenic microbes from the oral cavity, as well as ensures the in-depth ingrowth of the bone tissue, thus promoting the installation strength and fixation in the jaw bone.

The example of implementation of the third variant of the dental implant claimed is represented on FIGS. 7 to 8. The dental implant has the seat 5 for the dental prosthesis and biologically compatible metal porous zone 6 for contact with bone. The metal porous zone for contact with bone is made from the porous three-dimensional structure claimed as a complex three-dimensional construction 15 in accordance with preliminary obtained 3D-tomogram of the tooth for which replacement this implant is intended, the shape coincides exactly with the tooth root shape and sizes.

This complex three-dimensional construction 15 contains the longitudinal branched base 16 where the porous three-dimensional structure 1 is pressed to; the reinforcing element 2 is on the surface of the porous three-dimensional structure and the evenly located protrusions 3 are fixed on the external surface of the reinforcing element 2.

The ring head 8 made from the porous three-dimensional structure from polytetrafluoroethylene and intended for ingrowth of the gum tissues is situated over the construction 15 around the seat 5.

The head 8 is made, as described in the first example.

This third variant of the dental implant (FIG. 7 to 8) is to be manufactured and installed as follows.

One shall make 3D-tomography of the tooth to be removed.

One shall form the computer model of this tooth root in accordance with the 3D-tomogram of the tooth and form the three-dimensional model of the longitudinal branched base of the implant under the computer model.

Under the computer model of the tooth root one shall mill the mold using the CNC machine; then, in turn, one shall mold from, for example, polyurethane, the matrix which is close to the shape of the mentioned three-dimensional model of the tooth root but exceeds its sizes by, for example, 5 to 10%.

One shall mill the longitudinal branched base 16 with the CNC machine under the computer model of this base.

One shall install the obtained base in the formed matrix which is filled with titanium powder and, for example, by the hydrostatic pressing method [Vityaz] one shall form the porous three-dimensional structure claimed which shape and sizes coincide exactly with the shape and sizes of the tooth root to be replaced with this implant.

Then, when the implant of the tooth to be removed is ready, one shall remove this tooth and press the preliminarily manufactured implant in the jaw bone immediately after extraction of such tooth without arrest of bleeding in such a way that the outer surface of the head 8 coincides with the level of the soft tissues of the gum and shall stitch the soft tissues. The dental prosthesis is installed in the seat 5 in the base 7 after final engraftment of the implant.

Due to the fact that the biologically compatible metal zone contacting with the bone tissue is made as a three-dimensional porous structure 1 and the implant is installed without arrest of bleeding, blood surrounds the three-dimensional porous structure in its whole depth, and this accelerates ingrowth of the bone tissue in the whole depth of the mentioned three-dimensional porous structure, i.e. integration. Here the biologically compatible metal three-dimensional porous zone 1 is safely protected from damages by the reinforcing element 2, and the protrusions 3 function both as anchor elements and prevent the whole implant from displacement and, thus, ensure its primary stability.

In addition, the porous three-dimensional structure 1 is safely protected from ingress of infection from the oral cavity by means of the head 8 from polytetrafluoroethylene which has the porous three-dimensional structure ensuring ingrowth of the soft tissues of the gum.

Thus, the dental implant claimed safely protects the implantation area from ingress of pathogenic microbes from the oral cavity, as well as ensures the in-depth ingrowth of the bone tissue, thus promoting the installation strength and fixation in the jaw bone.

Achievement of the technical result claimed has been proved by the trials in accordance with the International Standard ASTM International F 1147-058 for compliance with the requirements of the Standard ISO-5832-3 (Implants for Surgery. Deformable Titanium-based Alloy). The Standard ASTM describes the method to test the tensile force of coatings, in particular, of metal porous coatings being in close contact with dense metal bases at room temperature.

For the trials the test sample have been manufactured, as stipulated by the Standard ASTM; each of the test samples consisted of the metal base and the porous structure applied to the base, under the present invention.

The trials carried out made under the Standard mentioned have shown the ultimate strength of the samples under this invention to be from 933 MPa till 950 MPa what significantly exceeds the value of 860 MPa as prescribed by the Standard ISO-5832-3. No chipping, burrs and structure detachment was observed.

Therefore, manufacturing of the porous structure according to the present invention allows achievement of the properties unachievable earlier: increased strength and rigidity, absence of structure detachment, chipping and burrs in the course of use and, thus, refutation of the opinion of [Karl E. MISH].

The manufacturing enables to fix of the porous structure both on the implant and the bone, arrange the blood flow through pores in anatomical direction, increase the strength of cohesion of the cone tissue with the porous structure.

What is claimed is:

1. A dental implant, comprising:
   a porous three-dimensional structure; and
   a reinforcing mesh disposed on an outer surface of the structure and having protrusions directed away from the structure, said mesh made from titanium, titanium alloy or titanium powder, wherein the protrusions have a form factor of a parallelpiped.

2. The dental implant of claim 1, wherein the reinforcing mesh is made from a titanium sheet or titanium wire.

3. The dental implant of claim 1, wherein an aperture size of the reinforcing mesh is no less than a maximal size of pores in the structure.

4. The dental implant of claim 1, wherein pores in the structure have sizes in a range from 150 to 300 μm.

5. The dental implant of claim 1, wherein the reinforcing mesh is pressed into the structure.

\* \* \* \* \*